United States Patent [19]

Eldridge

[11] 4,341,215

[45] Jul. 27, 1982

[54] ABSORBENT DEVICE

[75] Inventor: William T. Eldridge, Darien, Conn.

[73] Assignee: Tampax Incorporated, Lake Success, N.Y.

[21] Appl. No.: 184,120

[22] Filed: Sep. 4, 1980

[51] Int. Cl.³ .............................................. A61F 13/20
[52] U.S. Cl. .................................................. 128/285
[58] Field of Search .................... 128/284, 287, 290 R, 128/285

[56] References Cited

U.S. PATENT DOCUMENTS

| | | |
|---|---|---|
| 3,379,721 | 4/1968 | Reid . |
| 3,490,454 | 1/1970 | Goldfarb et al. ............... 128/285 |
| 3,589,364 | 6/1971 | Dean et al. . |
| 3,628,534 | 12/1971 | Donohue ........................ 128/285 |
| 3,639,259 | 2/1972 | Scarpelli . |
| 3,678,031 | 7/1972 | Schoggen . |
| 3,872,024 | 3/1975 | Hörger . |
| 3,900,030 | 8/1975 | Bashan ............................ 128/285 |
| 3,909,444 | 9/1975 | Anderson et al. . |
| 3,985,840 | 10/1976 | Hofacker . |
| 4,016,100 | 4/1977 | Suzuki et al. . |
| 4,024,073 | 5/1977 | Shimizu et al. . |
| 4,026,292 | 5/1977 | Hutchins et al. . |
| 4,028,290 | 6/1977 | Reid . |
| 4,055,180 | 10/1977 | Karami ............................ 128/284 |
| 4,089,800 | 5/1978 | Temple . |
| 4,104,214 | 8/1978 | Meierhoefer . |
| 4,107,288 | 8/1978 | Oppenheim et al. . |
| 4,131,648 | 12/1978 | Choi et al. . |
| 4,157,983 | 6/1979 | Golden . |
| 4,183,911 | 1/1980 | Smithies et al. . |

OTHER PUBLICATIONS

*Nonwovens Industry,* Silk, pp. 12, 38.

*Primary Examiner*—C. Fred Rosenbaum
*Attorney, Agent, or Firm*—Curtis, Morris & Safford

[57] ABSTRACT

An absorbent device for aqueous liquids, particularly useful as a catamenial tampon, e.g. of cotton or rayon fibers and a plurality of initially protectively-coated discrete portions of a super-absorbent material incorporated with the overall mass of absorbent material. Preferably a liquid soluble material surrounds and protectively encapsulates each discrete portion of super-absorbent material. The liquid soluble material of each encapsulated unit is designed to dissolve in the presence of different predetermined levels of menses to permit absorption of the menses by the super-absorbent material within respective encapsulated units. Accordingly, the greater the menstrual flow, the greater number of encapsulated units which become absorbent. The units may be microencapsulated. Trigger mechanisms other than solubility are contemplated for activating the absorbency of the discrete portions of super-absorbent material, when needed. At least 50% of the super-absorbent material is protectively encapsulated and preferably 75% to 95% is so protected.

25 Claims, 2 Drawing Figures

ABSORBENT DEVICE

BACKGROUND OF THE INVENTION

This invention relates to aqueous liquid absorbent devices and, more particularly, is directed to improved catamenial tampons having enhanced absorbency characteristics.

Most currently available catamenial tampons are made solely from cotton, rayon, or other cellulosic-based fibers. Such tampons are typically compacted and stored within a tampon applicator. Thus, when the tampon is ejected from the tampon applicator into the vaginal cavity, it is enveloped by the vaginal walls. Thus positioned, the tampon absorbs the menstrual flow to prevent leakage thereof from the vagina. During such absorption, the tampon gradually expands.

However, the flow characteristics of a significant number of individuals are such that the absorption capacity and the rates of absorption of such tampons are inconvenient for practical purposes. In other words, during heavy menstrual flow, even the best of the traditional cellulosic tampons, such as the long staple cotton tampons, may not be capable of sufficiently rapid absorption and also may well require inconveniently frequent replacement. Oversaturated, or bypassed, tampons can result in a leakage of the menses with a consequent discomfort and staining of the undergarments. Increasing the size of conventional cotton or similar tampons to increase capacity causes problems of insertion and withdrawal. The alternative of frequent daily changes is limiting of the user's activities and thus is highly undesirable.

Tampons incorporating a "super-absorbent" material (more fully defined below) have been used to varying degrees with some success in the last few years. Such tampons may include super-absorbent fibers incorporated with more traditional absorbent materials. These super-absorbent tampons can increase capacity on a percentage basis by better than 50%.

The high-capacity super-absorbent fibers act to reabsorb the menses from the other absorbent materials (as well as from other wetted surfaces). However, the super-absorbent fibers pull the menstrual flow from the other material without regard to the level of menstrual flow. Thus, during light or minimal flow, the highly absorbent nature of the tampon tends to dehydrate the vaginal tissue. This, of course, can be a source of considerable irritation and discomfort, particularly during withdrawal of the tampon. This discomfort may last for some time after removal of the tampon and even lead to difficulty in inserting the next tampon.

OBJECTS AND SUMMARY OF THE INVENTION

Accordingly, it is an object of this invention to provide a catamenial tampon with increased absorbency per unit volume that overcomes the above-described difficulties.

More particularly, it is an object of this invention to provide such a catamenial tampon wherein the available absorbency characteristics are dependent on the level of menstrual flow.

It is another object of this invention to provide a catamenial tampon which is designed to control the effectiveness of its super-absorbing agents relative to predetermined level(s) of menstrual flow.

It is still another object of this invention to provide a catamenial tampon which satisfactorily absorbs menses during heavy menstrual flow but which does not dehydrate the vaginal tissues during relatively light menstrual flow.

In accordance with a preferred embodiment of this invention, an absorbent device, illustratively described as a catamenial tampon, includes a fibrous absorbent mass of material, such as a cotton or rayon pad, and a plurality of discrete portions of a super-absorbent material incorporated among the fibrous absorbent material. A liquid soluble material surrounds and protectively encapsulates each discrete portion of super-absorbent material so as to form a plurality of encapsulated units with the super-absorbent material enclosed within each unit. The liquid soluble material of each encapsulated unit is designed to dissolve in the presence of different predetermined levels of menses to permit access between the super-absorbent material within respective encapsulated units and the menses. As the tampon absorbs more fluid, a greater number of super-absorbent units become available for absorbing the menses. Preferably as the super-absorbent material is activated, it never significantly reduces the wetness of the cotton pad portion of the tampon, but mainly just incrementally increases its absorptive capacity. Other alternatives are discussed below.

In this specification and the accompanying drawings, I have shown and described a preferred embodiment of my invention and have suggested various alternatives and modifications thereof; but it is to be understood that these are not intended to be exhaustive and that many other changes and modifications can be made within the scope of the invention. These suggestions herein are selected and included for purposes of illustration in order that others skilled in the art will more fully understand the invention and the principles thereof and will thus be enabled to modify it and embody it in a variety of forms, each as may be best suited to the conditions of a particular use.

DETAILED DESCRIPTION OF THE PREFERRED EMBODIMENTS

Figure 1:
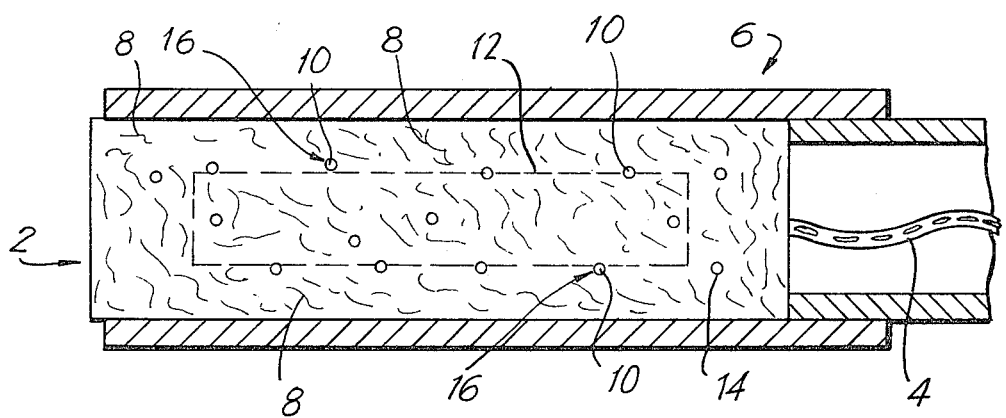
FIG. 1 is a schematic, longitudinal cross-sectional view of a preferred embodiment of a catamenial tampon according to this invention, shown in conjunction with a conventional tampon applicator.

Referring to FIG. 1, a catamenial tampon 2 according to this invention is shown in the form of an elongated cylinder and includes a withdrawal string 4 for removing the tampon after use. The tampon is shown inside a conventional tampon applicator 6.

Figure 2:
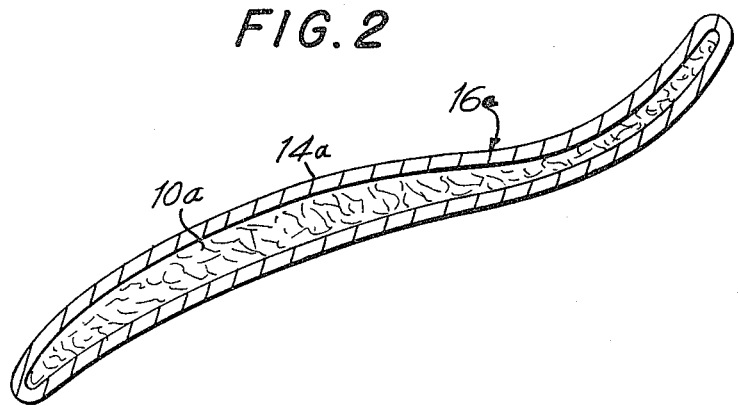
FIG. 2 is a blown-up schematic view of a portion of an alternative embodiment of an encapsulated unit including at least a single super-absorbent fiber which can be used with the tampon of FIG. 1.

Catamenial tampon 2 is comprised of a compressed pad of a fibrous absorbent material 8, preferably cotton or rayon. Alternatively, the mass of absorbent material 8 could be in some other form, such as absorbent foam particles as taught by U.S. Pat. No. 3,815,601. Interspersed between the particles of the absorbent material 8 are discrete portions 10 of a super-absorbent material (see for example the materials disclosed in U.S. Pat. No. 4,134,863, entitled "Highly Absorbent Graft Copolymers of Polyhydroxy Polymers, Acrylonitrile, and Acrylic Comonomers"). Alternatively in a simplified version, the super-absorbent material may be lumped together in a central portion of the tampon (shown by the dashed line 12 in FIG. 1). The super-absorbent material is shown in FIG. 1 as being granular and in FIG. 2 as being fibrous.

An encapsulating material 14 surrounds and protectively encapsulates each discrete portion of super-absorbent material 10 to form encapsulated units 16, as shown in FIG. 1. The units 16 may advantageously be formed by microencapsulation techniques. The units 16 should preferably be capable of withstanding pressure due to compaction of the fibrous absorbent material 8.

In the preferred embodiment, the encapsulating material 14 is impervious to the menses during periods of low flow, but is dissolved or permeable during a high or predetermined level of menstrual flow. During such low menstrual flow, the cotton or rayon fibers alone satisfactorily absorb the menses. However, during high menstrual flow, the encapsulating material 14 permits access of the menses for absorption by the super-absorbent material.

Preferably, the encapsulating material 14 is a liquid soluble material which is adapted to dissolve in the presence of such predetermined level of menses. For example, such liquid soluble material may consist of a material from the group of polyvinyl pyrrolidone, natural gums (Arabic, tragacanth, et cetera), and hydrolyzed graft polymerized starches, methyl cellulose, hydroxypropyl cellulose, cellulose acetate phthalate, hydroxypropyl methyl cellulose, hydroxypropyl methyl cellulose phthalate, polyethylene glycols, polyvinyl alcohol, and polyethylene oxide. In alternative embodiments, the encapsulating or protective means may be essentially impervious but may be rendered permeable by alternative triggering mechanisms. For example, it has been found that hydrophobic mineral oil as a practical matter over the typical maximum usage of a tampon (which will not often exceed 8 hours and rarely exceeds 12 hours) will inhibit the absorption of menses by super-absorbents, but that the rate of absorption increases with the level of menses present. Without in any way being bound by these theories, it is postulated that when an excess of menses is present in a tampon, the increased hydrostatic pressures overcome the hydrophobic tendencies of the mineral oil on the surface of the super-absorbent and succeed in forcing the menses into contact with the untreated interior of the super-absorbent. A further triggering mechanism involves a chemical reaction which would be supported by a predetermined minimum level of menses to change the character of the encapsulating barrier thus rendering it effectively permeable to the menses.

It may be preferable to free the super-absorbent material only in gradually increasing amounts corresponding to graduated increases in the level of menses. In this case, the encapsulating material 14 would be different for different discrete portions 10 so as to dissolve at different respective levels of menses. Thus, the liquid soluble material 14 of one or more encapsulated units 16 may be set to dissolve during the presence of a low level of menses. It is contemplated that the fibrous absorbent pad 8 could handle 25% of the rated capacity of the tampon before any of the super-absorbent material would be effectively available. Or alternatively, the super-absorbent material would be effectively activated only after the pad 8 had absorbed the equivalent of 1 gram of menses per 1 gram of the tampon. Other of the encapsulated units 16 might be set to dissolve only after the tampon had absorbed 2 grams of menses per gram of tampon, and still further encapsulated units might similarly be set to dissolve only after 3 grams of menses had been absorbed per gram of tampon. Preferably, the amount of super-absorbent material made accessible each time is less than the amount which would cause dehydration of tissues in contact with the tampon.

Since the encapsulating material does have the effect of inhibiting the rate of fluid absorption, it may be desirable to have some portion of the super-absorbent untreated. The untreated material will, of course, have a tendency to create the dry condition this invention is intended to avoid, but this may be necessary to avoid fluid bypass. To achieve proper balance between minimized dryness on the one hand and danger of bypass on the other, up to 50% of the super-absorbent may be untreated, with the preferred range being 5% to 25% untreated.

The tampon may include a water pervious overwrap or bag (not shown) as will be understood by those skilled in the art.

Super-absorbent materials have been incorporated into tampons in the form of alloyed copolymeric fibers. At least some, and optionally all, of the absorbent fibers of the tampon can be made up of such fibers. See U.S. Pat. No. 4,066,584 for a description of "Alloyed Fibers of Rayon and Copolymers of Acrylic and Methacrylic Acids" disclosed as useful for making tampons with increased absorbency.

According to another alternative embodiment of the present invention, the absorbent material 8 can be formed at least in part of such alloy fibers. At least a portion of such alloy fibers 10a will be treated with an encapsulating material 14a or with another functionally equivalent protective means.

It is contemplated that this invention in its broader aspects is useful for absorbent devices other than the catamenial tampon preferred embodiment described herein, for example for diapers, surgical dressings, and sanitary pads.

The term "super-absorbent" as used herein does not include the traditional tampon absorbents such as cotton, rayon, nor most ordinary sponges. This term as used herein and as understood by the industry would have an absorbency of at least several times that of cotton or rayon under similar conditions. Note that most super-absorbents, unlike cotton, rayon, or sponges, typically release water only with extreme difficulty when squeezed (even at relatively high liquid levels).

For purposes of comparison, a loose ball of cotton will absorb 24 to 25 times its weight of water, while super-absorbents under similar tests will absorb 200 to 300 times their own weight, with some claims for absorbency of more than 1,000 times their own weight (although in these latter cases the super-absorbents will pass into a gelatinous state making them impractical for use in tampons because of the difficulty of physically restraining the gelatinous mass, although they still hold liquid). In a better comparison, the average absorbency at failure of a cotton tampon would be in the range of 3.3 to 3.5 grams per gram weight of the tampon (with the upper and lower limits of failure being from 1 gram per gram to 8 grams per gram). When super-absorbents are incorporated, the average absorbency at failure increases to approximately 4.5 grams per gram, depending upon the super-absorbent. If the absorbency attributed to the super-absorbent is pro-rated over the amount of super-absorbent in the tampon, it can be calculated that the super-absorbent will have absorbed approximately 15 grams of water per gram of super-absorbent.

Note that the term "absorbent material" 8 is not necessarily exclusive of super-absorbent materials. The fibrous mass 8 might be made of the alloyed fibers discussed above. However, in the preferred embodiment, the absorbent material 8 would not include super-absorbent material, or at least would contain considerably less super-absorbent material per gram of the absorbent material 8 than would be contained in a gram of the discrete portion 10 containing super-absorbent material.

What is claimed is:

1. A catamenial tampon comprising:
   an open-structured mass of absorbent material;
   super-absorbent material, including at least one discrete portion thereof;
   encapsulating means using an encapsulating material for isolating at least 50% of the super-absorbent material from being wetted by an aqueous liquid, such as water or menses, in one or more of said discrete portions;
   each said encapsulated discrete portion being incorporated within said mass of absorbent material; and
   said encapsulating material being adapted in the presence of a relative excess of menses, and prior to saturation of said mass of absorbent material, to permit absorption of the excess menses by the super-absorbent material originally contained within such encapsulating means.

2. A catamenial tampon according to claim 1; wherein said encapsulating means is adapted to permit absorption by such super-absorbent material when in the presence of a predetermined level of menses.

3. A catamenial tampon according to claim 2; wherein said mass of absorbent material is fibrous.

4. A catamenial tampon according to claim 1; in which said encapsulating means comprise a liquid soluble material surrounding at least one said discrete portion of super-absorbent material so as to form at least one encapsulated unit with said super-absorbent material enclosed therein, said liquid soluble material being adapted to dissolve in the presence of said predetermined level of menses.

5. A catamenial tampon according to claim 4; in which said liquid soluble material consists of at least one material from the group consisting of polyvinyl pyrrolidone, natural gums, hydrolyzed graft polymerized starches, methyl cellulose, hydroxypropyl cellulose, cellulose acetate phthalate, hydroxypropyl methyl cellulose, hydroxy-propyl methyl cellulose phthalate, polyethylene glycols, polyvinyl alcohol, and polyethylene oxide.

6. A catamenial tampon according to claim 3; in which each said discrete portion of super-absorbent material is fibrous in form and each fibrous discrete portion is coated with a layer of said liquid soluble material.

7. A catamenial tampon according to claim 5; in which each said discrete portion of super-absorbent material is granular in form and each granular discrete portion is coated with a layer of said liquid soluble material.

8. A catamenial tampon according to claim 4; in which there are a plurality of discrete portions of said super-absorbent material protectively encapsulated by said liquid soluble material.

9. A catamenial tampon according to claim 8; in which at least some of said encapsulated units are adapted to permit absorption of menses at a different predetermined level of menses from the level at which other of the encapsulated units permit such absorption.

10. A catamenial tampon according to claim 3; in which said encapsulating means comprises microencapsulations of the super-absorbent material.

11. A catamenial tampon according to claim 10; in which said microencapsulated units are capable of withstanding pressure due to compaction of the fibrous absorbent material.

12. A catamenial tampon according to claim 3; in which said fibrous absorbent material is compacted and formed in an elongated substantially cylindrical configuration.

13. A catamenial tampon according to any one of claims 3 or 10; in which said mass of absorbent material is chosen from the group consisting of cotton and rayon.

14. A catamenial tampon according to claim 1, wherein the total absorbent capacity of the super-absorbent material rendered capable of menses absorption at any given level of menses is less than would significantly reduce the degree of wetness of the mass of fibrous absorbent materials.

15. A catamenial tampon according to any one of claims 6, 9, or 14, wherein said mass of absorbent material and each discrete portion of super-absorbent material comprise alloy fibers formed of a cellulose and of a super-absorbent.

16. A catamenial tampon according to claim 1, wherein the alloy fiber for each said discrete portion has a greater absorbency potential than that for the mass of absorbent material.

17. An absorbent device for aqueous liquids comprising:
   an open-structured mass of absorbent material;
   super-absorbent material, including at least one discrete portion thereof;
   protective means for substantially isolating from aqueous liquids at least 50% of said super-absorbent material in said one or more discrete portions;
   each said isolated discrete portion being incorporated into said mass of absorbent material; and
   said protective means being adapted initially to prevent access of aqueous liquids to each said discrete portion and being further adapted to permit access thereto in response to at least one predetermined triggering condition.

18. A device as claimed in claim 1 for use as a catamenial tampon, wherein there are a plurality of discrete portions formed of super-absorbent fibers and said protective means is a coating of hydrophobic mineral oil applied in an amount sufficient essentially to block access of low levels of menses to said discrete portions but to pass menses into said discrete portions when the mass of absorbent material has been substantially wetted sufficiently thereby to satisfy the triggering condition whereby the menses is forced past the mineral oil barrier.

19. A device as claimed in claim 1 for use as a catamenial tampon, wherein a predetermined level of menses is the triggering condition for providing a reaction medium to support a chemical reaction for modifying the protective means to permit access of menses to said discrete portion.

20. A device as claimed in any one of claims 1 to 12, 14, 16 to 18 or 19, wherein the amount of super-absorbent material which is encapsulated ranges from 75% to 95%.

21. A device as claimed in claim 13 wherein the amount of super-absorbent material which is encapsulated ranges from 75% to 95%.

22. A device as claimed in claim 15 wherein the amount of super-absorbent material which is encapsulated ranges from 75% to 95%.

23. A device as claimed in any one of claims 1 to 12, 14, 16 to 18 or 19, wherein 100% of the super-absorbent material is encapsulated.

24. A device as claimed in claim 13, wherein 100% of the super-absorbent material is encapsulated.

25. A device as claimed in claim 15, wherein 100% of the super-absorbent material is encapsulated.

* * * * *

UNITED STATES PATENT AND TRADEMARK OFFICE
CERTIFICATE OF CORRECTION

PATENT NO. : 4,341,215
DATED : July 27, 1982
INVENTOR(S) : William T. Eldridge

It is certified that error appears in the above—identified patent and that said Letters Patent is hereby corrected as shown below:

Claim 18, line 1, change "1" to --17--.

Claim 19, line 1, change "1" to --17--.

Signed and Sealed this

Twenth-eighth Day of September 1982

|SEAL|

Attest:

GERALD J. MOSSINGHOFF

Attesting Officer     Commissioner of Patents and Trademarks